(12) United States Patent
Rajala (10) Patent No.: US 8,720,518 B2
(45) Date of Patent: May 13, 2014

(54) APPARATUS FOR BONDING RIBBON IN A NONLINEAR PATTERN TO A WEB

(75) Inventor: Gregory J. Rajala, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 595 days.

(21) Appl. No.: 12/971,971

(22) Filed: Dec. 17, 2010

(65) Prior Publication Data

US 2012/0152441 A1 Jun. 21, 2012

(51) Int. Cl.
*A61F 13/15* (2006.01)

(52) U.S. Cl.
CPC .................................. *A61F 13/15609* (2013.01)
USPC .................... 156/440; 242/615.2; 242/615.21

(58) Field of Classification Search
None
See application file for complete search history.

(56) References Cited

U.S. PATENT DOCUMENTS

| | | | |
|---|---|---|---|
| 4,041,203 A | 8/1977 | Brock et al. | |
| 4,281,619 A | 8/1981 | Frick | |
| 4,293,367 A | 10/1981 | Klasek et al. | |
| 4,675,068 A | 6/1987 | Lundmark | |
| 4,909,880 A * | 3/1990 | Kittelson et al. | 156/189 |
| 4,915,767 A | 4/1990 | Rajala et al. | |
| 4,917,746 A | 4/1990 | Kons | |
| 5,147,487 A | 9/1992 | Nomura et al. | |
| 5,221,390 A | 6/1993 | Persson | |
| 5,236,539 A | 8/1993 | Rogberg | |
| 5,275,676 A | 1/1994 | Rooyakkers | |
| 5,525,175 A | 6/1996 | Blenke et al. | |
| 5,660,657 A | 8/1997 | Rajala | |
| 5,766,411 A | 6/1998 | Wilson | |
| 5,779,689 A | 7/1998 | Pfeifer et al. | |
| 6,217,690 B1 | 4/2001 | Rajala | |
| 6,287,409 B1 | 9/2001 | Stephany | |
| 6,589,149 B1 * | 7/2003 | VanEperen et al. | 493/380 |
| 6,890,630 B2 | 5/2005 | Franklin et al. | |
| 7,045,031 B2 * | 5/2006 | Popp et al. | 156/176 |
| 7,048,991 B2 | 5/2006 | Franklin et al. | |
| 2002/0023706 A1 | 2/2002 | Vogt et al. | |
| 2005/0000628 A1 | 1/2005 | Norrby | |
| 2008/0105384 A1 | 5/2008 | Eckstein | |
| 2009/0020211 A1 | 1/2009 | Andrews | |
| 2009/0157036 A1 | 6/2009 | Ponomarenko | |
| 2010/0200145 A1 | 8/2010 | Yamamoto | |
| 2012/0090779 A1 * | 4/2012 | Nakamura et al. | 156/324 |

FOREIGN PATENT DOCUMENTS

| | | |
|---|---|---|
| EP | 1842516 A1 | 10/2007 |
| JP | 7255777 A | 1/1995 |
| WO | 9623477 A2 | 8/1996 |
| WO | 2004078083 A1 | 2/2004 |
| WO | WO 2010113610 A1 * | 10/2010 |

OTHER PUBLICATIONS

International Search Report and Written Opinion for PCT/IB2011/054983 dated Jun. 15, 2012; 14 pages.

* cited by examiner

*Primary Examiner* — Barbara J Musser
(74) *Attorney, Agent, or Firm* — Armstrong Teasdale LLP (57) ABSTRACT

A ribbon applicator configured to guide ribbon to a web includes a support structure and a cantilever arm supported by the support structure. The cantilever arm is moveable through a range of motion relative to the support structure. A guide roller guides the ribbon onto the web. The guide roller is pivotally mounted on the cantilever arm for pivotal movement of the guide roller with respect to the cantilever arm.

13 Claims, 9 Drawing Sheets

APPARATUS FOR BONDING RIBBON IN A NONLINEAR PATTERN TO A WEB

BACKGROUND

The field of the invention relates generally to apparatus for and methods of bonding ribbon to a web and more particularly to apparatus for and methods of adhesively bonding ribbon in a nonlinear pattern to a moving web.

BRIEF DESCRIPTION

Absorbent articles, such as disposable diapers, training pants, adult incontinence articles and the like, generally include several different components that are bonded together. Typical absorbent articles include a bodyside liner, an outer cover, and an absorbent core disposed between the liner and outer cover. Besides the liner, the outer cover, and the absorbent core, typical absorbent articles also include a number of discrete components, e.g., fasteners, waist elastics, leg elastics. These discrete components of the article are often bonded to the bodyside liner and/or the outer cover. For example, it is known to adhesively bond leg elastics in a curved pattern to a continuous web of outer cover material or bodyside liner material.

However, known techniques for bonding leg elastics to a web moving at high line speeds are often limited in the amount of displacement (e.g., the amount of amplitude in a curved pattern) that can be achieved. Thus, leg elastics in known absorbent articles produced at high line speeds are often straight or relatively straight. The leakage protection and the aesthetic appearance of known absorbent articles can be improved, however, by incorporating leg elastics with significant curvature along their lengths.

Known efforts to place leg elastics with significant amounts of displacement (i.e., curvature) onto a web at high line speeds have been unsuccessful. These efforts have resulted in leg elastics being placed off target. Moreover, the deviation of the applied leg elastics from the target was not always the same.

Moreover, known curved leg elastics application technology requires that the leg elastics be sandwiched between two webs using an adhesive with both webs being at least as wide as the width of the elastic pattern, which is the distance between the transverse extents of the leg elastics as it is applied to the web. Furthermore, the adhesive is applied in a continuous band and at a width that is substantially equal to the width of the elastic pattern. In larger absorbent articles, e.g., adult incontinence briefs, the width of the elastic pattern can be more than 127 millimeters.

The adhesive not in direct contact with the leg elastics and one of the two webs between which the leg elastics are bonded serve no purpose during use of the article and, therefore, is waste. In adult incontinence briefs, for example, this waste can amount to more than 3% of the material costs.

As a result, it is desirable to provide an apparatus and method for bonding a ribbon in a nonlinear manner to a web wherein a relatively minimal amount of adhesive is used to bond the ribbon to the web.

BRIEF DESCRIPTION

In one aspect, a ribbon applicator is configured to guide ribbon to a web. The applicator generally comprises a support structure and a cantilever arm supported by the support structure and moveable through a range of motion relative to the support structure. A guide roller is provided for guiding the ribbon onto the web. The guide roller is pivotally mounted on the cantilever arm for pivotal movement of the guide roller with respect to the cantilever arm.

In another aspect, apparatus for bonding ribbon in a nonlinear pattern to a web generally comprises a web source for feeding the web to the apparatus. An adhesive applicator is provided for applying adhesive in a nonlinear pattern to the web. A ribbon applicator is configured to deliver and place the ribbon in a nonlinear pattern on the web such that the ribbon overlies and covers the adhesive applied thereto.

In yet another aspect, a method of bonding a ribbon to a web generally comprises feeding a web to an adhesive applicator. An adhesive is applied in a nonlinear pattern to the web with the adhesive applicator. The adhesive applied to the web has a width. A ribbon is overlaid on the adhesive such that the ribbon covers the adhesive. The ribbon has a width that is one of equal to and greater than the width of the adhesive.

BRIEF DESCRIPTION OF THE DRAWINGS

Corresponding reference characters indicate corresponding parts throughout the drawings.

DETAILED DESCRIPTION OF THE DRAWINGS

Figure 1:
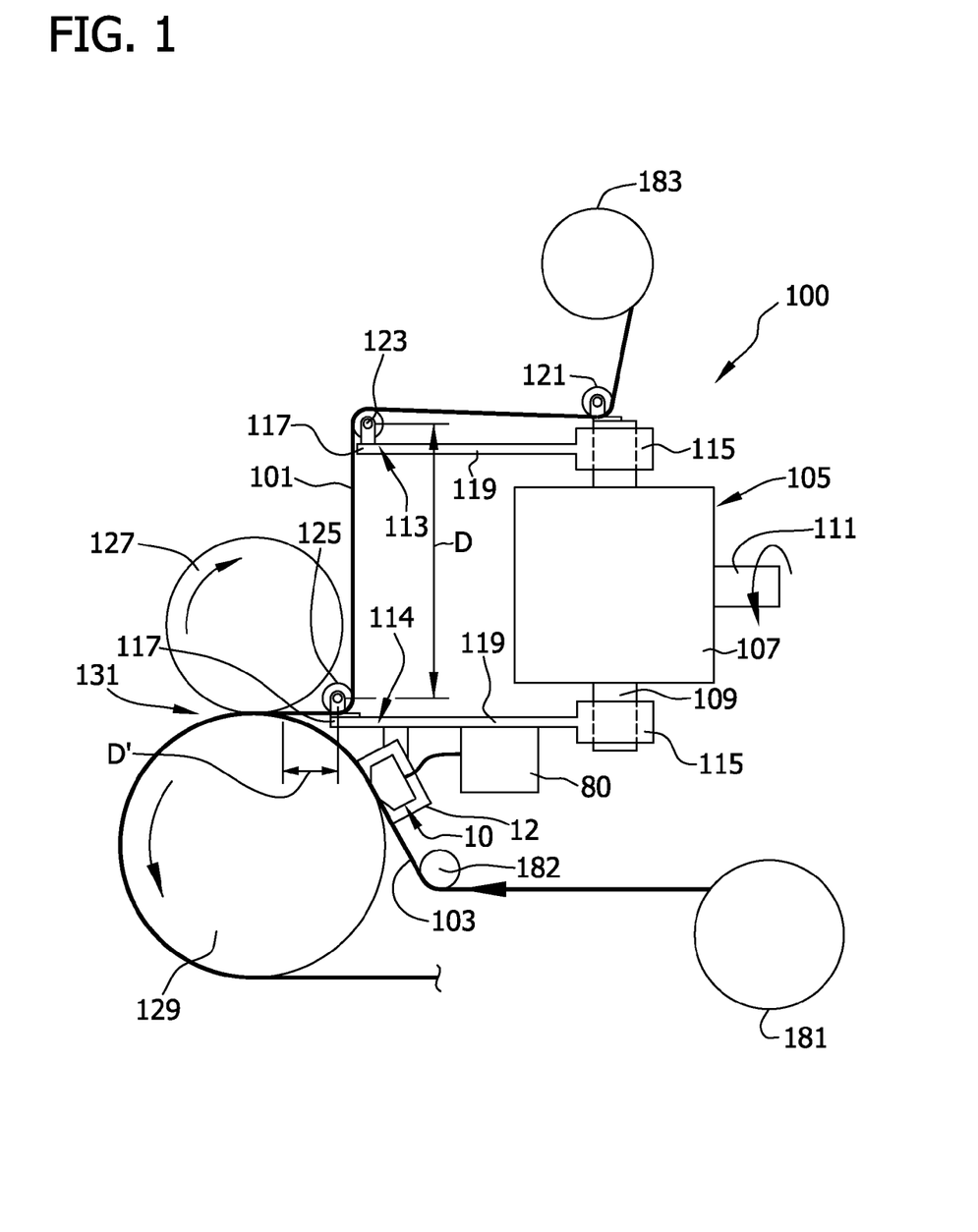
FIG. 1 is a schematic of one embodiment of an apparatus for adhesively bonding a ribbon in a nonlinear pattern to a web.

With reference now to the Figures and in particular to FIG. 1, an apparatus for bonding ribbon 101 in a nonlinear pattern to a web 103 is indicated generally at 100. The apparatus 100 includes a ribbon applicator, indicated generally at 105, configured to deliver and apply the ribbon 101 on the web 103. As seen in FIG. 1, the ribbon applicator 105 of the illustrated embodiment comprises a cam box 107 (broadly, a support structure), a pivot shaft 109 supported by and extending vertically through the cam box, and a drive shaft 111 extending horizontally into the cam box and operatively connected to the vertical pivot shaft.

Upper and lower cantilever arms, indicated generally at 113 and 114 respectively, are affixed to the pivot shaft 109. As illustrated in FIG. 1, the upper cantilever arm 113 is disposed above the cam box 107 and the lower cantilever arm 114 is disposed below the cam box. Each of the cantilever arms 113, 114 includes an attachment end 115, a free end 117, and an intermediate portion 119 extending between the attachment end and the free end. The attachment end 115 is secured to the pivot shaft 109 such that rotation of the pivot shaft results in conjoint rotation of the cantilever arms 113, 114.

In one suitable embodiment, the lower cantilever arm 114 has a length that is slightly longer than the upper cantilever arm 113 (FIG. 1). For example, in the illustrated embodiment, the lower cantilever arm 114 has a length of about 10 inches and the illustrated upper cantilever arm 113 has a length of about 8.5 inches.

With reference still to FIG. 1, the ribbon applicator 105 further includes three guide rollers 121, 123, 125. As seen in FIG. 1, a first guide roller 121 is mounted on an upper end of the pivot shaft. The second and third guide rollers 123, 125 are mounted, respectively, to the ends 117 of the cantilever arms 113, 114. That is, the second guide roller 123 is mounted to the end 117 of the upper cantilever arm 113 and the third guide roller 125 is mounted to the end of the lower cantilever arm 114.

Figure 7:
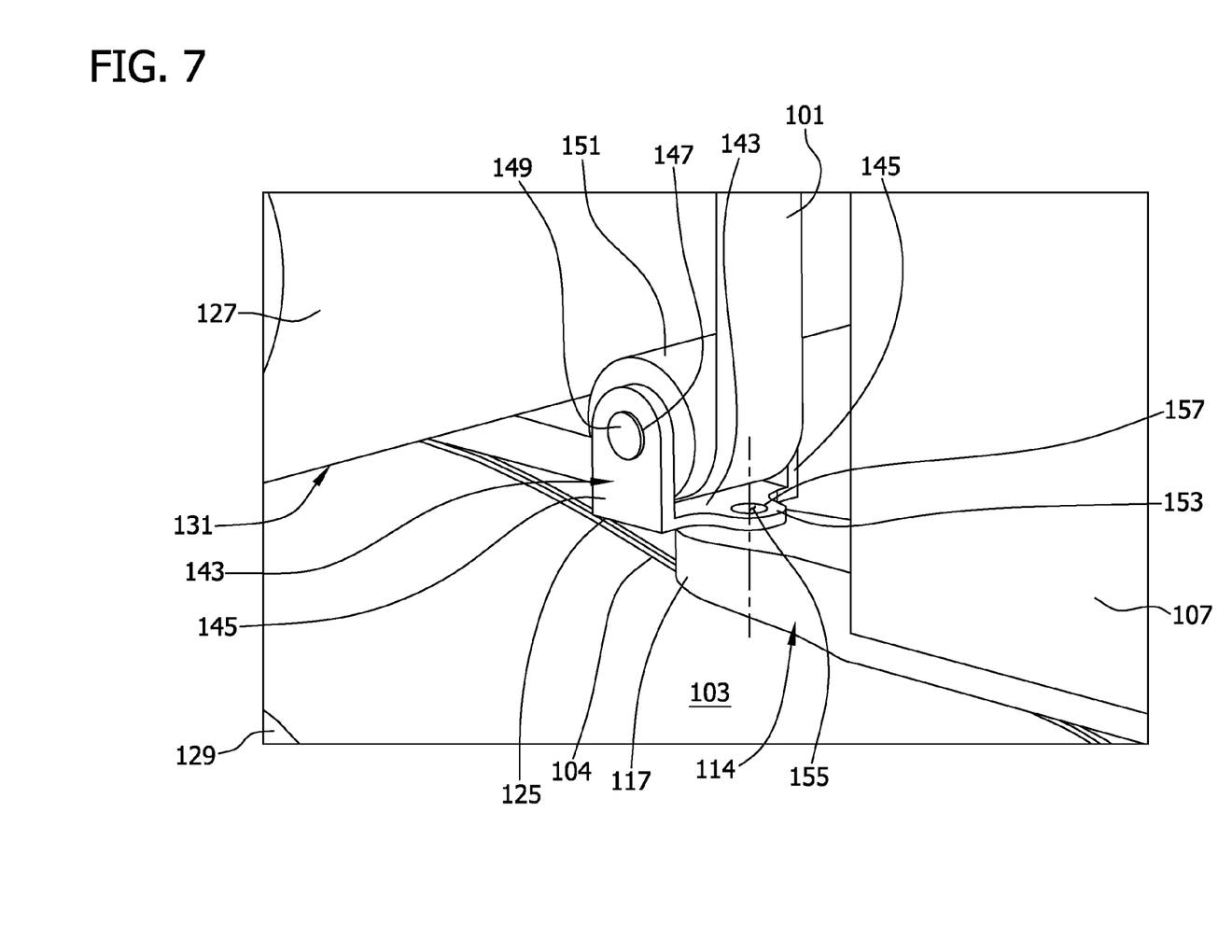
FIG. 7 is an enlarged perspective illustrating one guide roller of the apparatus guiding the ribbon onto the web and into a nip.

In the illustrated embodiment, the third guide roller 125 is pivotally mounted to the free end 117 of the lower cantilever arm 114. As seen in FIG. 7, the third guide roller 125 comprises a bracket, indicated generally at 141, having a base plate 143 and a pair of sidewalls 145 extending upward from the base plate. Each of the sidewalls 145 includes an aperture 147 (only one aperture being illustrated in FIG. 7) for receiving and thereby mounting a shaft 149 to the bracket 141. A roller 151 is rotatable mounted on the shaft 149. The base plate 143 of the bracket 143 includes a tab 153 having an opening 155 therein. A pivot pin 157 is received through the opening 155 in the tab 153 to pivotally mount the third guide roller 125 to the lower cantilever arm 114. That is, the third guide roller 125 can pivot with respect to the lower cantilever arm 114 about the pivot pin 157. In the illustrated embodiment, the roller 151 is a cylindrical roller but it is contemplated that the roller can have other suitable shapes (i.e., spool-like, hourglass, football, truncated football) without departing from the scope of this invention.

With reference again to FIG. 1, the apparatus 100 further comprises a pair of anvil rolls 127, 129 that collectively define a nip 131. The anvil rolls 127, 129 are configured to apply a predetermined pressure to the ribbon 101 and web 103 as they pass through the nip 131. The pressure applied to the ribbon 101 and web 103 at nip 131 can be varied by changing the relative positions of the rolls 127, 129.

The rolls 127, 129 rotate in opposite directions, as indicated by the arrows in FIG. 1, to draw the ribbon 101 and web 103 into the nip 131. Each of the rolls 127, 129 is operable independently from the other and are driven (i.e., rotated) by suitable drive means, such as, for example, electric motors (not shown). As a result, the rotational speed of the rolls 127, 129 (as measured at the rolls' outer surface) can be the same or can differ. That is, the rolls 127, 129 can operate at the same or different rotational speeds. It is contemplated that only one of the rolls 127, 129 may be rotatable in an embodiment wherein one of the rolls is a stationary roll.

Each of the rolls 127, 129 in the illustrated embodiment is cylindrical with a smooth outer surface. It is contemplated, however, that one or both of the rolls 127, 129 can have shapes other than cylindrical and that the outer surface may be other than smooth (i.e., patterned). In addition, the rolls 127, 129 can be formed from any suitable, durable material, such as, for example, hardened metal or steel, hardened rubber, resin-treated cotton, or polyurethane. The rolls 127, 129 can be formed from the same material or different materials. In the illustrated embodiment, for example, the roll 127 is a steel roll covered with silicone rubber having a 55A to 70A Shore Durometer to facilitate release of any adhesive that may contact the roll, and the roll 129 is a hardened steel roll.

The temperature of the outer surface of at least one of the rolls 127, 129 can be controlled to heat or cool the respective roll. In one suitable embodiment, the outer surface of at least one of the rolls 127, 129 is cooled to inhibit adhesive from bonding to or otherwise adhering to the outer surface of the roll. In another suitable embodiment, the outer surface of at least one of the rolls 127, 129 is heated to enhance bonding between the ribbon 101 and the web 103.

The apparatus 100 also comprises an adhesive applicator 10 for applying adhesive in a nonlinear pattern to the web 103. It is understood that any suitable adhesive applicator can be used by apply the adhesive to the web 103. It is contemplated, however, that adhesive can be applied to the ribbon 101 instead of or in addition to the web 103.

The ribbon 101 can be formed from any suitable material including, but not limited to, wovens, nonwovens, films, foams, or combinations thereof. The material can be stretchable, non-stretchable, elastic or inelastic. In one suitable embodiment, the ribbon 101 is an elastomeric material suitable for use as leg elastics in absorbent articles.

Figure 2:
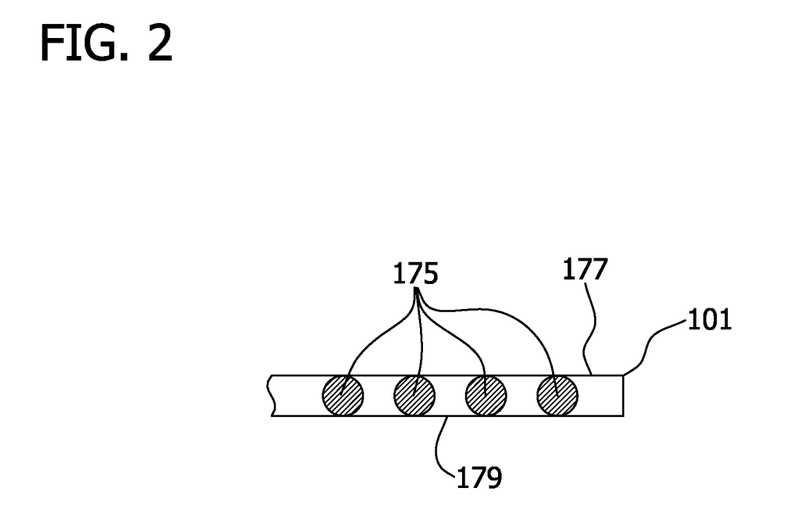
FIG. 2 is a vertical cross-section of one suitable embodiment of the ribbon.

As seen in FIG. 2, the illustrated ribbon 101 is an elastomeric laminate comprising a plurality of LYCRA strands 175 sandwiched between a first sheet 177 and a second sheet 179. In the illustrated embodiment, the first and second sheets 177, 179 are defined by a single-piece of material that is folded about its length. It is contemplated, however, that the first and second sheets 177, 179 can be separate pieces of material. It is also contemplated that one of the first and second sheets 177, 179 can be omitted. In other suitable embodiments, the ribbon 101 can be formed from spunbond laminates (SBL), necked bonded laminates (NBL), and spunbond-meltblown-spunbond (SMS) nonwovens, which are also suitable materials for use as leg elastics in absorbent articles.

In one suitable embodiment, the web 103 comprises a material suitable for use as an outer cover of absorbent articles. As one example, the outer cover material may be a multi-layered laminate structure to provide desired levels of extensibility as well as liquid impermeability and vapor permeability. For example, the outer cover may be a two-layer construction, including an outer layer constructed of a vapor permeable material and an inner layer constructed of a liquid impermeable material, with the two layers being secured together by a suitable adhesive. It is understood, however, that the outer cover material can have more or fewer layers (e.g., a single layer plastic film).

In another embodiment, the web 103 comprises a material suitable for use as a bodyside liner of absorbent articles. The bodyside liner material can be a material that is suitably pliable, soft feeling, and nonirritating to the wearer's skin. The bodyside liner material should be sufficiently porous to be liquid permeable to thereby permit liquid (e.g., urine) to readily penetrate through its thickness. Suitable bodyside liner materials can be manufactured from a wide selection of web materials.

Figure 3:
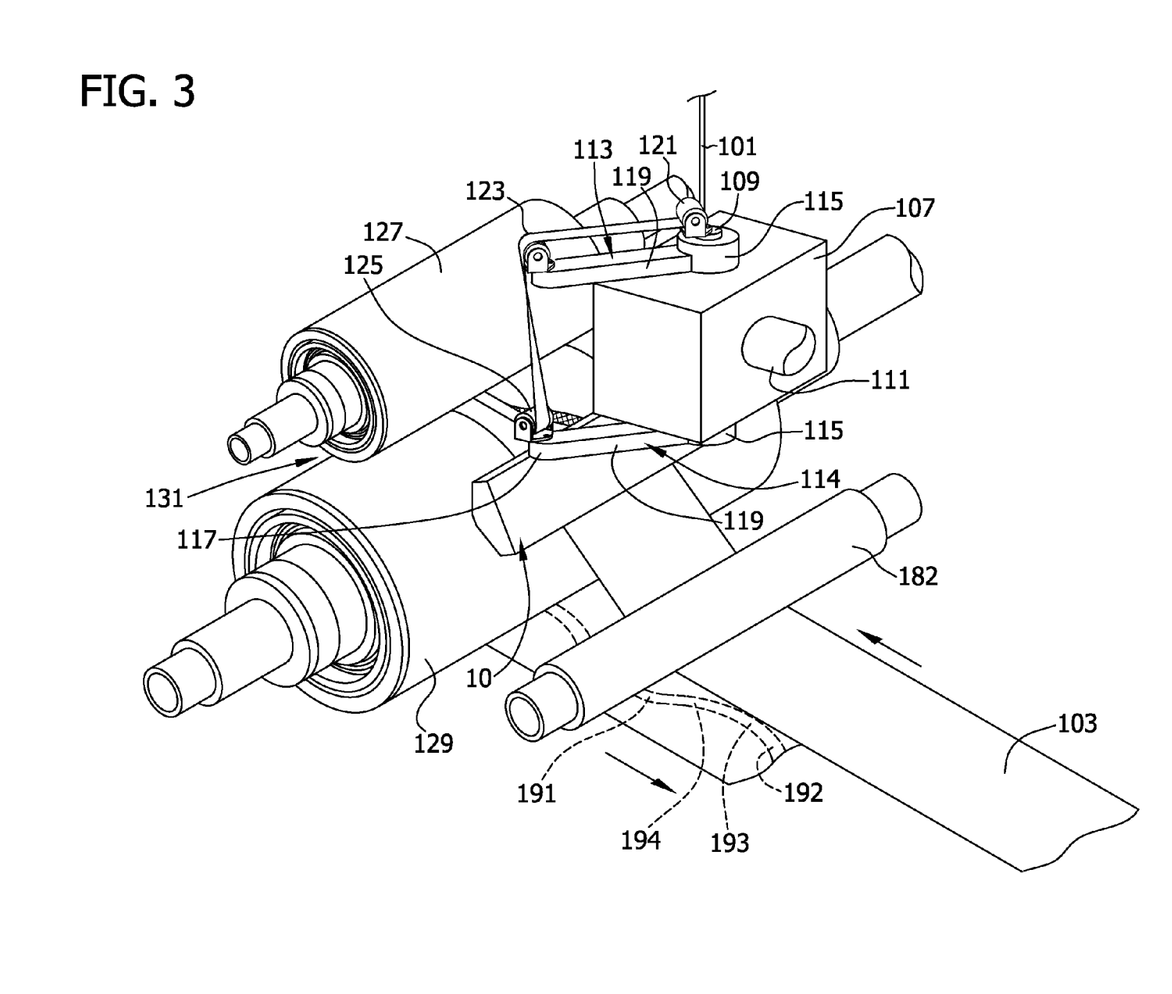
FIGS. 3-6 are sequential perspectives illustrating the apparatus adhesively bonding the ribbon in a nonlinear pattern to the web while the web is moving at a high line speed.

In use, the web 103 is fed from a web roll 181 (or other suitable web source) past a roller 182 to the adhesive applicator 10 where adhesive 104 is applied in a nonlinear pattern to the web (FIGS. 1 and 3). In one suitable embodiment, the web 103 is traveling at a high line speed. As used herein, high line speed refers to a line speed greater than about 600 feet per minute.

The adhesive 104 is heated to a suitable temperature and driven to the adhesive applicator 10 at a suitable pressure by an adhesive source 80. In an "on position" of the adhesive applicator 10, adhesive 104 is driven through a housing 12 of the adhesive applicator and onto the web 103 in the desired nonlinear pattern of adhesive 104 (e.g., a curved pattern).

After the adhesive 104 is applied to the web 103 by the adhesive applicator 10, the web is fed to the nip 131 defined by the pair of opposed rolls 127, 129. As described in more detail below, the ribbon 101 is laid over the adhesive 104 applied to the web 103 prior to the web entering the nip 131.

As seen in FIG. 1, the ribbon 101 is fed to the ribbon applicator 105 by a ribbon roll 183 (or other suitable ribbon source). The ribbon applicator 105 applies the ribbon 101 to the web 103 in a nonlinear pattern that matches the nonlinear pattern along which the adhesive 104 was applied to the web such that the ribbon overlies and covers the adhesive. More specifically, the ribbon 101 is fed past the first guide roller 121 and generally parallel to the upper cantilever arm 113 to the second guide roller 123. From the second guide roller 123, the web 103 is fed downward (as viewed in FIG. 1) to the pivotable third guide roller 125.

With reference now to FIGS. 3-6, the ribbon 101 is fed through the guide rollers 121, 123, 125 under tension which causes the ribbon to stretch. In one suitable embodiment, the ribbon 101 is under about 0.1 pound to about 1 pound per CD inch of tension. It is understood, however, that the tension force applied to ribbon 101 can be different that disclosed herein.

The third guide roller 125 is spaced from the second guide roller 123 by a distance D (FIG. 1). The distance D is selected to facilitate proper alignment of the ribbon 101 as it is fed to the third guide roller 125 and to inhibit twisting or bunching of the ribbon during movement of the third guide roller relative to the second guide roller 123, which is mounted to the upper cantilever arm 113 in a non-pivoting manner. In one suitable configuration, the distance between the third guide roller 125 and the second guide roller 123 is approximately 10 times the width of the ribbon.

In the illustrated embodiment, the ribbon 101 is wrapped around approximately 90 degrees of the circumference of each of the guide rollers 121, 123, 125. In other words, the ribbon 101 extends around about a quarter of the circumference of the guide rollers 121, 123, 125 as it passes over the respective guide roller. It is understood that the ribbon 101 can be wrapped around more or less of the circumference of one or more of the guide rollers 121, 123, 125 by changing the angle at which the ribbon is fed to the respective guide roller (i.e., the approach angle of the ribbon).

The placement of the ribbon 101 onto the web 103 can be accurately controlled by the ribbon applicator 105. Specifically, the placement of the ribbon 101 on the web 103 can be controlled by rotating the drive shaft 111 either clockwise or counterclockwise and at variable speeds by a suitable drive source (not shown). Suitable drive sources include, for example, lineshafts, AC or DC variable speed drives and motors, and servo motors. The rotational movement of the drive shaft 111 is transferred into pivotal movement of the pivot shaft 109 within the cam box 107.

Pivotal movement of the pivot shaft 109 causes conjoint pivoting of the upper and lower cantilever arms 113, 114. Since the ribbon 101 is fed through the first, second, and third guide rollers 121, 123, 125 which are mounted on the pivot shaft 109 and cantilevers arms 113, the portion of the ribbon received by the ribbon applicator 105 pivots with the pivot shaft and cantilever arms.

Figure 8:
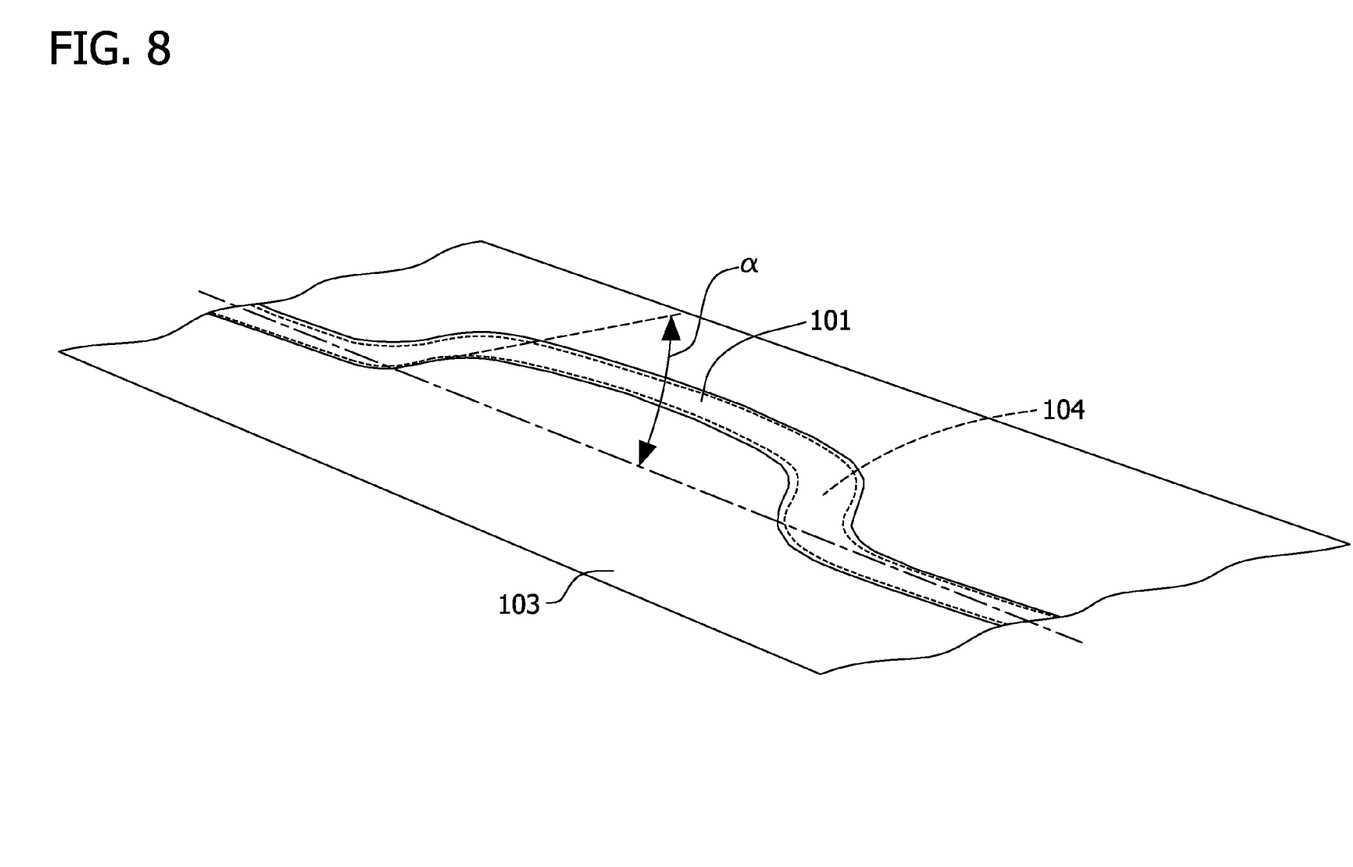
FIG. 8 is a perspective of a portion of the web showing the ribbon adhered thereto in a nonlinear pattern.

In one suitable embodiment, the ribbon applicator 105 is adapted to apply the ribbon 101 to the web 103 with significant curvature while the web is traveling at high line speeds. As used herein, "significant curvature" refers to the acute angle α defined by a line tangent to the elastic curve and the longitudinal centerline of the web that is greater than about 45 degrees (FIG. 8).

In the illustrated embodiment, the drive source rotationally drives the drive shaft 111 in a counterclockwise direction (FIG. 1). The rate at which the drive shaft rotates the drive shaft 111 is variable and is used to control the rate at which the ribbon applicator 105 and, more specifically, the lower cantilever arm 114 and thus, the third guide roller 24 pivots. It is understood, however, that the suitable drive source can drive the drive shaft 111 at a generally constant rotational rate and/or in the clockwise direction.

The third guide roller 125, which is mounted to the lower cantilever arm 114, moves conjointly with the pivot shaft 109 through a suitable range of motion. As mentioned, the third guide roller 125 directs placement of the ribbon 101 onto the web 103. Thus, the operation of the suitable drive source of the drive shaft 111 can be selectively controlled to control the placement pattern of the ribbon 101 onto the web 103. In the illustrated embodiment, for example, the drive source is paused (i.e., stopped) or slowed considerably in FIG. 3 such that the ribbon 101 is placed onto the web 103 in a generally straight line to form a first generally straight segment 191 of the ribbon.

The rotation rate of the drive shaft 111 is then increased by the drive source to form a first curved portion 192 of the ribbon 101. During this increase in rotation rate, the drive shaft 111 causes the pivot shaft 109 to rotate in a clockwise direction (as indicated by arrow 195 in FIG. 4). Pivoting the pivot shaft 109 conjointly pivots the upper and lower cantilever arms 113, 114, the first guide roller 121, and the second guide roller 123. In addition, pivoting movement of the lower cantilever arm 114 conjointly pivots the third guide roller 125.

Figure 4:
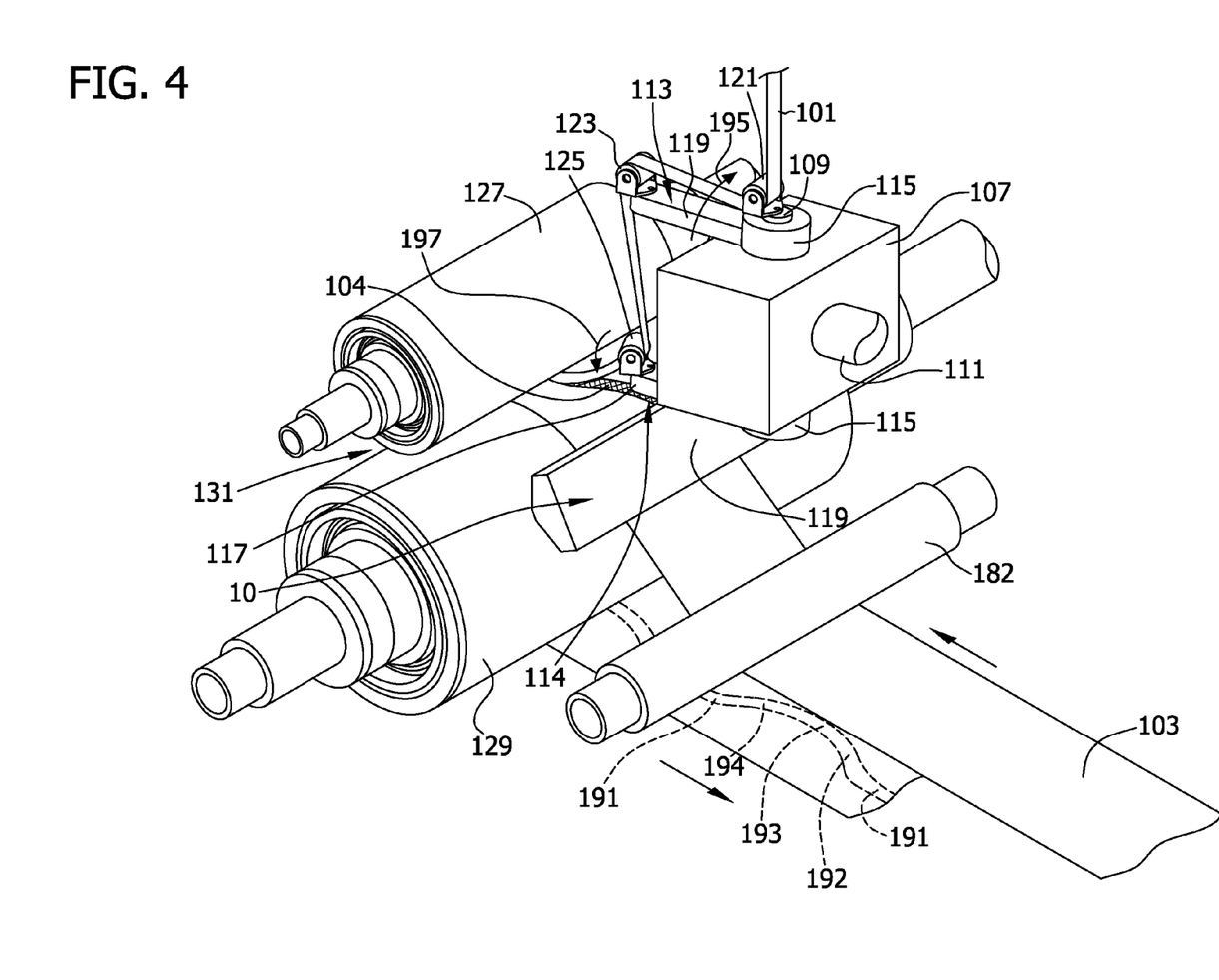

Since the third guide roller 125 is pivotally mounted on the lower cantilever arm 114, pivoting movement of the lower cantilever arm also causes the third guide roller 125 to pivot about the pivot pin 157 in the counterclockwise direction (i.e., opposite the pivotal movement of the pivot shaft 109), which is indicated by arrow 197 in FIG. 4. As the pivot shaft 109 pivots in the counterclockwise direction, the third guide roller 125 moves with the lower cantilever arm 114 which directs the ribbon 101 onto the web 103 in a curved pattern.

Figure 5:
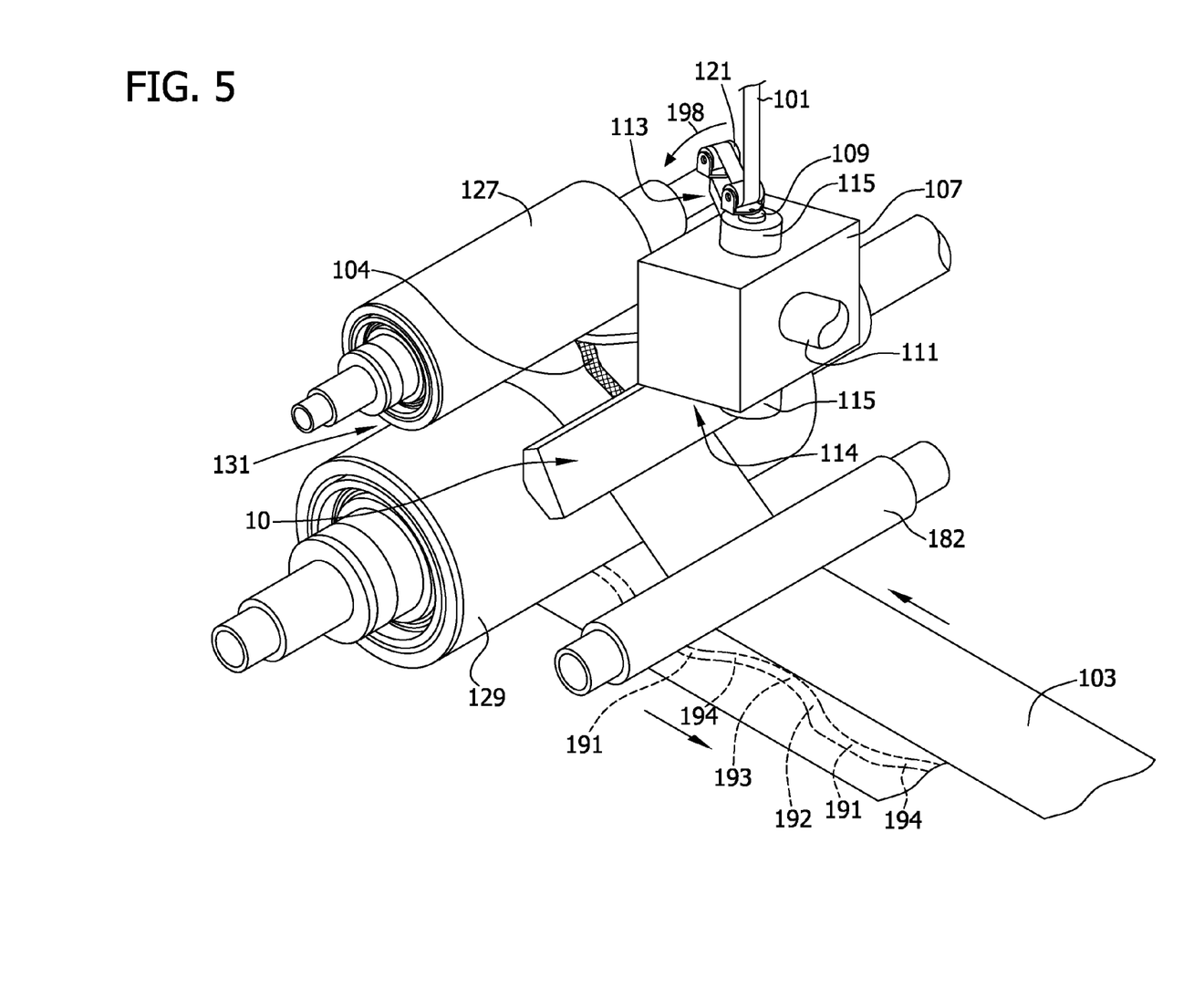
Figure 6:
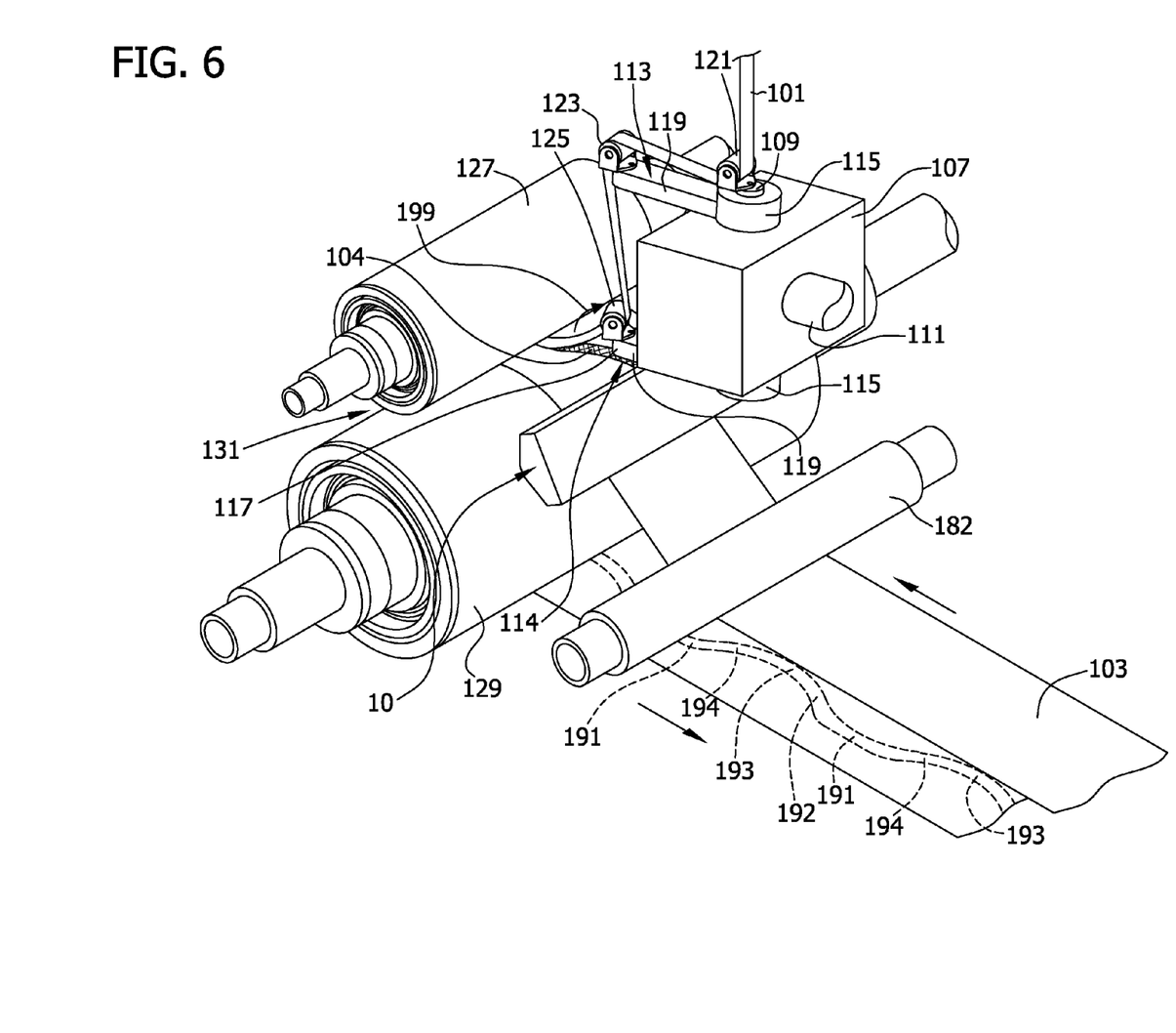

The pivot shaft 109 and thereby the lower cantilever arm 114 and the third guide roller 125 continues to pivot towards the right as viewed in FIG. 4 until the pivot shaft reaches the position illustrated in FIG. 5. At this position, the upper and lower cantilever arms 113, 114 are located in their right most position as viewed in FIG. 5. As a result, the third guide roller 125 and thereby the ribbon 101 are also in their right most position as viewed in the Figures and the ribbon is attached to the web to form an apex 123 of the curved ribbon.

At this location, the pivot shaft 109 changes directions and begins to pivot in the counterclockwise direction (as indicated by arrow 198 in FIG. 5. As a result, the upper and lower cantilever arms 113, 114 are pivoted in the counterclockwise direction along with the pivot shaft 109. The third guide roller 125 moves conjointly with the lower cantilever arm 114. In addition, the third guide roller 125 pivots about the pivot pin 157 in a clockwise direction (as indicated by arrow 199 in FIG. 6) with respect to the lower cantilever arm 114. This movement of the lower cantilever arm 114 and the third guide roller 125 creates a second generally curved portion 194 in the ribbon 101 as it is applied to the web 103.

FIGS. 3-6 collectively illustrate one full cycle of the ribbon applicator 105. In the illustrated embodiment, the ribbon 101 is applied to the web 103 in a generally sinusoidal pattern. It is understood, however, that the patterns of the ribbon 101 on the web 103 can be different than those illustrated herein.

After the ribbon 101 is overlaid on the adhesive 104 applied to the web 103, the ribbon 101 and the web 103 are pulled into the nip 131 by the rotation of the anvil rolls 127, 129. The rolls 127, 129 apply a predetermined pressure to the ribbon 101, the adhesive 104 and the web 103 as they pass through the nip 131 to facilitate adhesive bonding of the ribbon to the web.

In one suitable embodiment, a distance D' between the third guide roller 125 and the nip 131 is minimized to inhibit misalignment of the ribbon 101 relative to the web 103 before the ribbon is adhesively bonded to the web (FIG. 1). Suitably, the distance D' between the third guide roller 125 and the nip 131 is less than about 60 millimeters and suitable between about 20 millimeters and about 50 millimeters.

One suitable embodiment of the resulting composite (i.e., the web 103 having the ribbon 101 adhered thereto by adhesive 104) is illustrated in FIG. 8. As seen therein, the ribbon 101 has a width that is greater than a width of the adhesive 104. It is contemplated that the widths of the ribbon 101 and adhesive 104 can be substantially equal.

The composite may be used in the manufacture of absorbent articles (e.g., diapers, training pants, inconstancy articles). In one particularly suitable configuration, the web 103 can be used to form outer covers of absorbent articles and the ribbon 103 can be used to form leg elastics of the absorbent articles. One such absorbent article is illustrated in FIG. 9 in the form of an incontinence garment 200.

Figure 9:
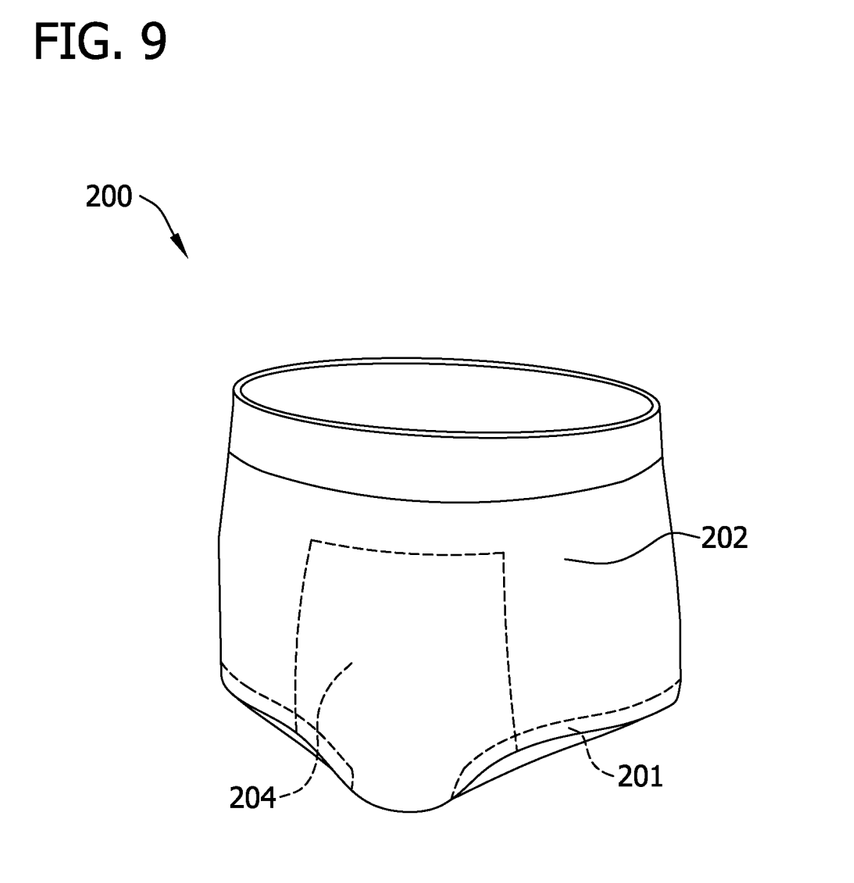
FIG. 9 is a perspective of one embodiment of an absorbent article in the form of an incontinence garment.

As seen in FIG. 9, the incontinence garment 200 comprises an outer cover 202, an absorbent core 204, and leg elastics 201. The outer cover 202 is made from the web 103 and the leg elastics are defined by the ribbon 101. It is understood that the garment 200 can include numerous other components (e.g., a bodyside liner, fasteners) than those illustrated and described herein.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements. Moreover, the use of "top", "bottom", "above", "below" and variations of these terms is made for convenience, and does not require any particular orientation of the components.

As various changes could be made in the above without departing from the scope of the invention, it is intended that all matter contained in the above description and shown in the accompanying drawings shall be interpreted as illustrative and not in a limiting sense.

What is claimed is:

1. A ribbon applicator configured to guide ribbon to a web, the applicator comprising:
    a support structure;
    a cantilever arm supported by the support structure and moveable through a range of motion relative to the support structure; and
    a guide roller for guiding the ribbon onto the web, the guide roller being pivotally mounted on the cantilever arm for pivotal movement of the guide roller with respect to the cantilever arm, wherein pivotal movement of the guide roller is dependent on movement of the cantilever arm.

2. The ribbon applicator as set forth in claim 1 wherein movement of the cantilever arm in one direction causes the guide roller to pivot in a generally opposite direction.

3. The ribbon applicator as set forth in claim 1 further comprising a pivot shaft, the cantilever arm being mounted to and extending outward from the pivot shaft.

4. The ribbon applicator as set forth in claim 3 wherein the cantilever arm comprises an attachment end affixed to the pivot shaft, a free end, and an intermediate portion extending between the attachment end and the free end, the guide roller being mounted to the cantilever arm adjacent the free end.

5. The ribbon applicator as set forth in claim 3 further comprises a drive shaft operatively connected to the pivot shaft.

6. The ribbon applicator as set forth in claim 5 wherein the support structure comprises a cam box for operatively connecting the drive shaft to the pivot shaft.

7. The ribbon applicator as set forth in claim 1 wherein the guide roller comprises a bracket, a shaft supported by the bracket, and a roller rotatable mounted on the shaft, the bracket being pivotally mounted to the cantilever arm via a pivot pin.

8. The ribbon applicator as set forth in claim 1 wherein the cantilever arm has a length greater than about 10 inches.

9. Apparatus for bonding ribbon in a nonlinear pattern to a web, the apparatus comprising:
    a web source for feeding the web to the apparatus;
    an adhesive applicator for applying adhesive in a nonlinear pattern to the web; and
    the ribbon applicator set forth in claim 1, the ribbon applicator being configured to deliver and place the ribbon in a nonlinear pattern on the web such that the ribbon overlies and covers the adhesive applied thereto.

10. The apparatus as set forth in claim 9 wherein movement of the cantilever arm in a first direction causes the guide roller to pivot in a direction that is generally counter to the first direction.

11. The apparatus as set forth in claim 10 wherein the guide roller is pivotally mounted to the cantilever arm via a pivot pin.

12. The apparatus as set forth in claim 9 further comprising a pivot shaft, the cantilever arm comprising an attachment end affixed to the pivot shaft, a free end, and an intermediate portion extending between the attachment end and the free end, the guide roller being mounted to the cantilever arm adjacent the free end.

13. The apparatus as set forth in claim 12 wherein the cantilever arm has a length of approximately 10 inches.

* * * * *